United States Patent
Colborn et al.

(10) Patent No.: US 11,878,166 B2
(45) Date of Patent: Jan. 23, 2024

(54) PERIPHERAL NERVE STIMULATION FOR RLS OR PLMD WITH SENSORS FOR MONITORING OF SLEEP-RELATED DATA

(71) Applicant: Noctrix Health, Inc., Pleasanton, CA (US)

(72) Inventors: John Craig Colborn, Magnolia, TX (US); Jonathan David Charlesworth, San Francisco, CA (US); Shriram Raghunathan, Castro Valley, CA (US)

(73) Assignee: NOCTRIX HEALTH, INC., Pleasanton, CA (US)

( * ) Notice: Subject to any disclaimer, the term of this patent is extended or adjusted under 35 U.S.C. 154(b) by 0 days.

(21) Appl. No.: 17/987,471

(22) Filed: Nov. 15, 2022

(65) Prior Publication Data

US 2023/0149711 A1     May 18, 2023

Related U.S. Application Data

(60) Provisional application No. 63/279,774, filed on Nov. 16, 2021.

(51) Int. Cl.
*A61N 1/36* (2006.01)
*A61M 5/172* (2006.01)
*A61N 1/04* (2006.01)

(52) U.S. Cl.
CPC ....... *A61N 1/36031* (2017.08); *A61M 5/1723* (2013.01); *A61N 1/0456* (2013.01)

(58) Field of Classification Search
CPC ............. A61N 1/36031; A61N 1/0456; A61M 5/1723
See application file for complete search history.

(56) References Cited

U.S. PATENT DOCUMENTS

| | | | |
|---|---|---|---|
| 2009/0221943 A1* | 9/2009 | Burbank | A61H 1/0266 601/46 |
| 2014/0057232 A1* | 2/2014 | Wetmore | G09B 19/00 600/28 |
| 2016/0354604 A1 | 12/2016 | Kent | |
| 2017/0135633 A1* | 5/2017 | Connor | A61N 1/36557 |
| 2019/0083784 A1* | 3/2019 | Raghunathan | A61B 5/4082 |
| 2020/0338347 A1 | 10/2020 | John et al. | |

FOREIGN PATENT DOCUMENTS

| | | |
|---|---|---|
| WO | 2021084478 | 5/2021 |
| WO | WO-2023091405 A1 | 5/2023 |

OTHER PUBLICATIONS

"International Application Serial No. PCT US2022 049949, International Search Report dated Feb. 17, 2023", 6 pgs.
"International Application Serial No. PCT US2022 049949, Written Opinion dated Feb. 17, 2023", 9 pgs.

* cited by examiner

*Primary Examiner* — Amanda K Hulbert
*Assistant Examiner* — Philip C Edwards
(74) *Attorney, Agent, or Firm* — SCHWEGMAN LUNDBERG & WOESSNER, P.A.

(57) ABSTRACT

A system for monitoring or treating RLS or PLMD can include or use a leg-wearable electrostimulation device for acquiring auxiliary data from a subject at a first leg location at which the device is worn, the first leg-wearable electrostimulation device including or using a first neurostimulation delivery device, an impedance sensor configured for determining an impedance via the first and second skin electrodes, and an auxiliary sensor configured for detecting the auxiliary data of the first leg location at which the device is worn.

21 Claims, 6 Drawing Sheets

PERIPHERAL NERVE STIMULATION FOR RLS OR PLMD WITH SENSORS FOR MONITORING OF SLEEP-RELATED DATA

CLAIM OF PRIORITY

This application claims priority to U.S. Provisional Application Ser. No. 63/279,774, filed on Nov. 16, 2021, which is incorporated by reference herein in its entirety, and the benefit of priority of which is claimed herein.

TECHNICAL FIELD

This document pertains generally, but not by way of limitation, to neurostimulation devices, and more particularly to systems and methods for charging the devices for providing recurrent electrostimulation therapy sessions.

BACKGROUND

Electrical nerve stimulation can be used to treat one or more conditions, such as chronic or acute pain, epilepsy, depression, bladder disorders, or inflammatory disorders. Certain neurological disorders can be attributed to overactivity of sensory or other peripheral nerve fibers which can disrupt quality of life, and/or the processing of such neural activity in the brain. Restless Legs Syndrome (RLS) and Periodic Limb/Leg Movement Disorder (PLMD) are two such neurological conditions that can significantly affect sleep in human patients. RLS (which can also be called Willis-Ekbom Disease (WED)) patients can experience uncomfortable tingling sensations in their lower limbs (legs) and, less frequently in the upper limbs (arms). RLS is characterized by an uncontrollable urge to move the affected limb(s). Such sensations can often be temporarily relieved by moving the limb voluntarily but doing so can interfere with the RLS patient's ability to fall asleep. PLMD patients can experience spontaneous movements of the lower legs during periods of sleep, which can cause the PLMD patient to wake up. RLS can be a debilitating sleep disorder and can be comorbid with other sleep disorders such as insomnia or sleep apnea syndrome (SAS).

SUMMARY

The present inventors have recognized, among other things, a technique to help reduce the effects of restless leg syndrome or other sleep disorders. A wearable electrostimulation device can be applied a subject's leg at or near a nerve target. The wearable electrostimulation device can include or use auxiliary sensors to collect data corresponding such as to the subject's heart rate, oxygenation, or leg movement during a sleep session. Also, an auxiliary component such as a charger for the wearable device can be used such as to collect data corresponding to a sleep environment of the subject.

Collected data can be used such as to help a clinician prescribe treatments to sleep disorders, such as to help a clinician decide, e.g., when to apply the therapy, when to stop applying a therapy, or when to restart applying therapy. Several modalities of data collection can be included in a therapy system. This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

The present techniques can help improve efficiency or effectiveness of treating a sleeping disorder such as RLS or PLMD, such as by issuing neural electrostimulation to a particular subject while using auxiliary components of an electrostimulation system to determine a quality of sleep of the subject during use of the electrostimulation system. In an example of sleep therapy such as electrostimulation therapy, a treatment routine or schedule can be prescribed for the subject by a sleep professional such as a clinician or sleep coach. A challenge of treating individuals with sleeping disorders is that few mechanisms exist for field research into the subject's native sleep routine. The sleep professional must rely on lab research of the subject, which can often be conducted in conditions which exacerbate causes of the sleep disorder, or the professional must rely on the subject's own account of sleep patterns and sleep environment. Further, it is especially difficult for the sleep professional or the subject to gain insight into symptoms exhibited by the subject during sleep in their native sleep environment, since the subject is unconscious, and the sleep professional is not present.

Subjects can vary in their response to medical treatments of sleep disorders. Thus, an approach to treatment using data-driven personalization of care can improve individual patient outcomes and to reduce individual or global treatment costs or treatment efforts. Compared to pharmaceutical therapies, electrical neurostimulation therapies have a particularly large potential for benefiting from personalization because such electrostimulation therapies are not necessarily monolithic. Instead, nerve stimulation can be optimized or adjusted, such as by programmatically adjusting one or more of the parameters of the electrical neurostimulation. The present inventors have conceived of a system for treating or monitoring sleep disorders by supplying electrostimulation to a subject along with detecting one or more sleep parameters associated to lack of sleep quality or a sleep disorder of the subject. The system can modify an electrostimulation protocol based on feedback associated with trends in sleep quality or sleep patterns detected by the system. The present inventors have also recognized, among other things, that a closed-loop or similar system that can adjust or optimize treatment quickly, e.g., using automation, thus improving individual patient treatment outcomes and reducing a cost of treatment.

Figure 1:
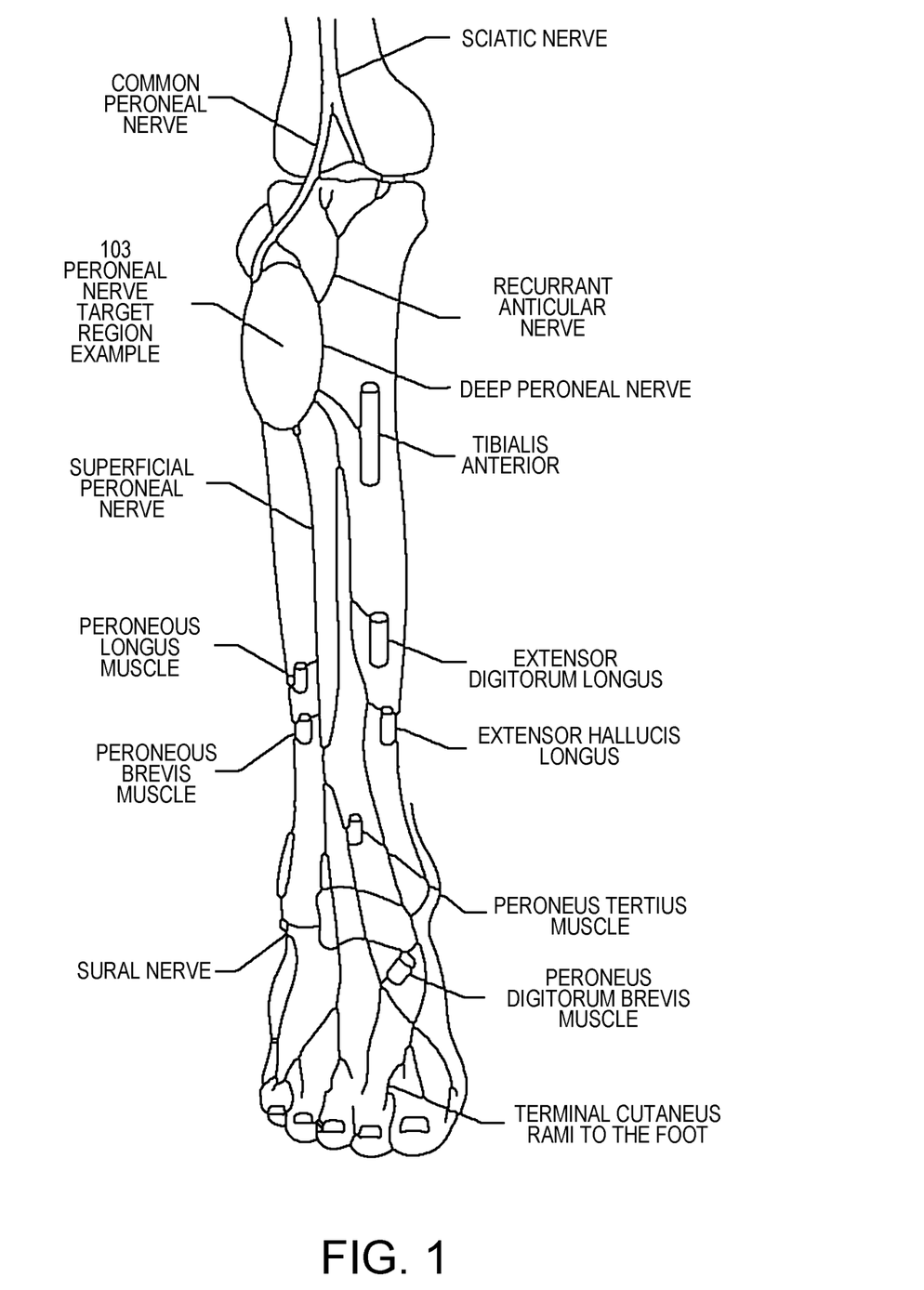
FIG. 1 depicts an example of a wearable external electrostimulation device shown located in proximity to a targeted region of a targeted peroneal nerve.

FIG. 1 depicts an example of a wearable external electrostimulation device shown located in close proximity to a targeted region 103 of a targeted peroneal nerve, such as at an anterior or lateral location just below the subject's knee, such as over a portion of the deep peroneal nerve. The wearable external electrostimulation device can be alternatively or additionally located at an even more inferiorly located region on the lower leg, such as over a portion of a superficial peroneal nerve, such as can innervate one or more parts of the tibialis anterior muscle. The superficial peroneal nerve and its direct peripherally extending branches and the sural nerve and its direct peripherally extending branches are the primary sensory nerves innervating this region of the leg. Therefore, such nerve locations are prime targets for RLS electrostimulation therapy. The present techniques can also include one or more specified selected nerve targets including such as a sural nerve, or a femoral nerve.

In an example depicted in FIG. 1 at least one electrode can be placed at the peroneal nerve target location, such as externally on the skin directly above or as close to possible to the superficial peroneal nerve. At least one electrode can be located directly below the bone landmark of the fibula in the outside of the knee below the lateral collateral ligament, or within 1 to 2 inches of the same. A second electrode may be located such that there is at least 1 inch of separation from the edge of the first electrode to the edge of the second electrode. The second electrode can be placed either along the length of the peroneal nerve, e.g., further down the leg, or the second electrode can be placed directly over the tibia, such as at about 1 to 2 inches below the first electrode. In an example, this second electrode can be located directly opposing the first electrode, to the inside of the knee, directly below the medial collateral ligament on the side of the tibia. The electrostimulation field may then be varied, such as to extend between a smaller or longer distance, such as to decrease sensory perception by the patient, if desired. In an example, two separate or different electrostimulation fields can be applied, such as by using the second electrode on the tibia as the common return electrode, such as can create a modulated electrostimulation field across the leg below the knee.

Figure 2A:
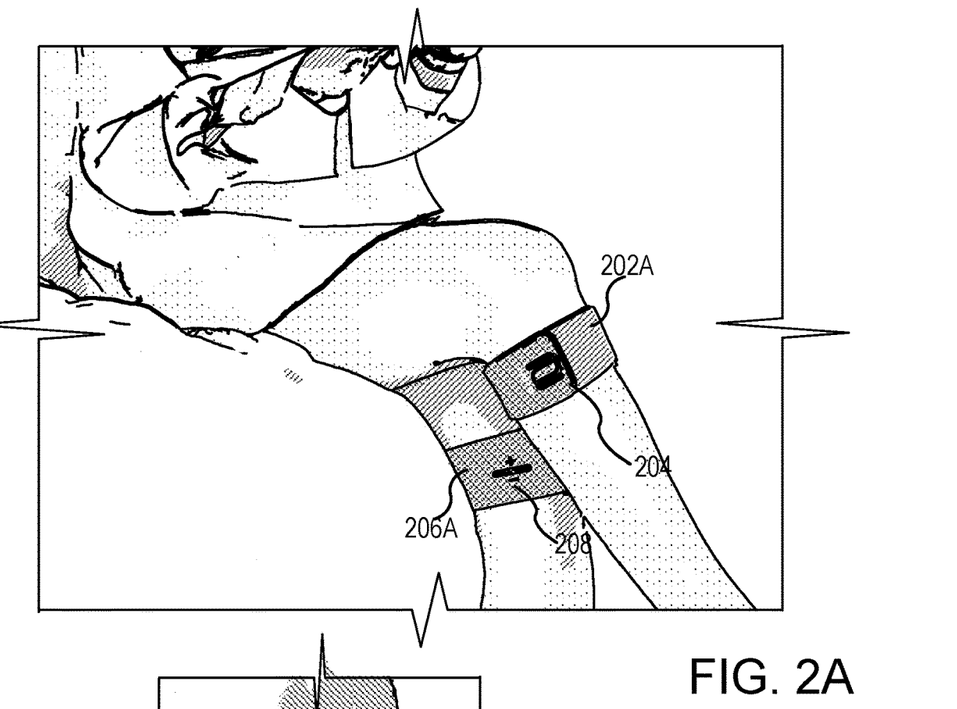
FIG. 2A depicts an example of a leg-wearable electrostimulation device in use on at a subject leg location.
Figure 2B:
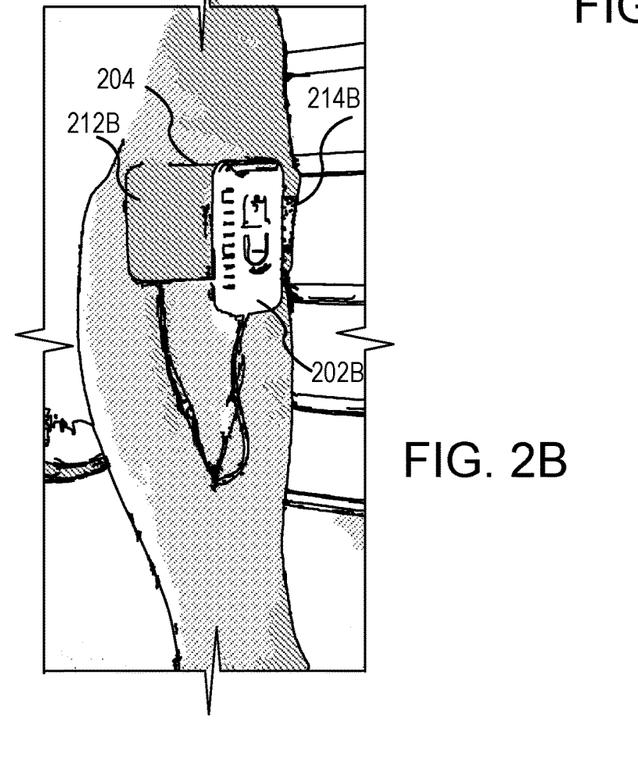
FIG. 2B depicts an example of a leg-wearable electrostimulation device in use on at a subject leg location.

FIG. 2A and FIG. 2B depict an example of a leg-wearable electrostimulation device in use on at a subject leg location. For example, as depicted in FIG. 2A, a first leg-wearable electrostimulation device 202A and a second leg-wearable electrostimulation device 202B can be worn by the subject bilaterally on each leg at respective first and second leg locations. In an example, the leg-wearable electrostimulation device can obtain a two or more electrodes for delivering transcutaneous electrostimulation. As described above with respect to FIG. 1, the leg-wearable electrostimulation device can be attached or held to one of the first leg location 204 and second leg location 208, at a respective nerve target. While described herein as a leg-wearable electrostimulation device, the device can be sized and shaped to be able to be attached or held to one of several body locations of the subject, e.g., a leg, arm, foot, waist, neck, head, or chest of the subject. In an example depicted by FIG. 2A, the wearable electrostimulation devices 202A, and 206A can include or use a strap, sleeve, band, or clamp to help hold the electrodes to the skin of the subject. Also, as depicted in 2B, each wearable electrostimulation device can adhere to its corresponding leg location and be held thereto. Alternatively or additionally, as depicted in FIG. 2B, the wearable electrostimulation device can be sufficiently wearable on the skin surface of the patient by adhesion forces of the electrodes alone without the need for additional features to help hold the device to the subject.

Figure 3A:
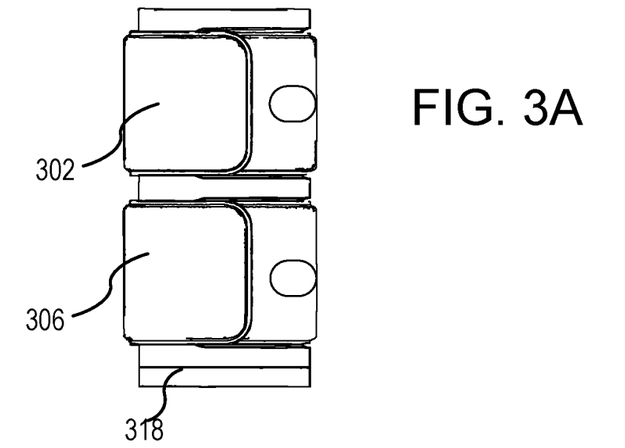
FIG. 3A depicts a pair of an example of leg-wearable electrostimulation devices wrapped around a local interface device.

FIG. 3A depicts a pair of an example of leg-wearable electrostimulation devices 302 & 306 wrapped around a local interface device 318. The local interface device 318 a type docking station or charging station for each of the leg-wearable electrostimulation devices 302 & 306 and can be communicatively coupled thereto. The local interface device 318 can reside near a subject during sleep, such as on a nightstand or dresser or any other location near the sleep environment of the subject. The local interface device 318 can include or use at least one environment sensor for collecting environment data of a sleep environment of the subject. The environment sensor can collect data associated with luminosity, temperature, audio, or motion of a bedmate or other movement in the sleep environment of the subject. The local interface device 318 can include or use battery charging circuitry for charging a rechargeable battery of either of the first leg-wearable electrostimulation device 302 and the second leg-wearable electrostimulation device 306. The docking station charge the first and second leg-wearable electrostimulation devices 302 and 306 concurrently or simultaneously. The local interface device 318 can provide a safe or hygienic place to store the leg-wearable electrostimulation devices 302 and 306 such as to preserve a hydrogel material of the devices 302 and 306 or to minimize accumulation of dust and dirt near the electrodes. The local interface device 318 can include or use or be communicatively coupled to a processor or controller circuitry. The processor circuitry can receive a user input such as communications from a user interface (UI). The UI can include or use switches, buttons, knobs, touch panels, status LEDs, or display screens such as to enable user interaction for performing electrostimulation therapy. The display, status LEDs, or other similar components can be capable of displaying or indicating user data, test outcomes, or instructions. In one example the display can be an LCD screen embedded in either of the wearable electrostimulation. Alternatively or additionally, the user can interact with the leg-wearable electrostimulation device by means of the software application on a remote device such as a computer or a mobile phone.

Figure 3B:
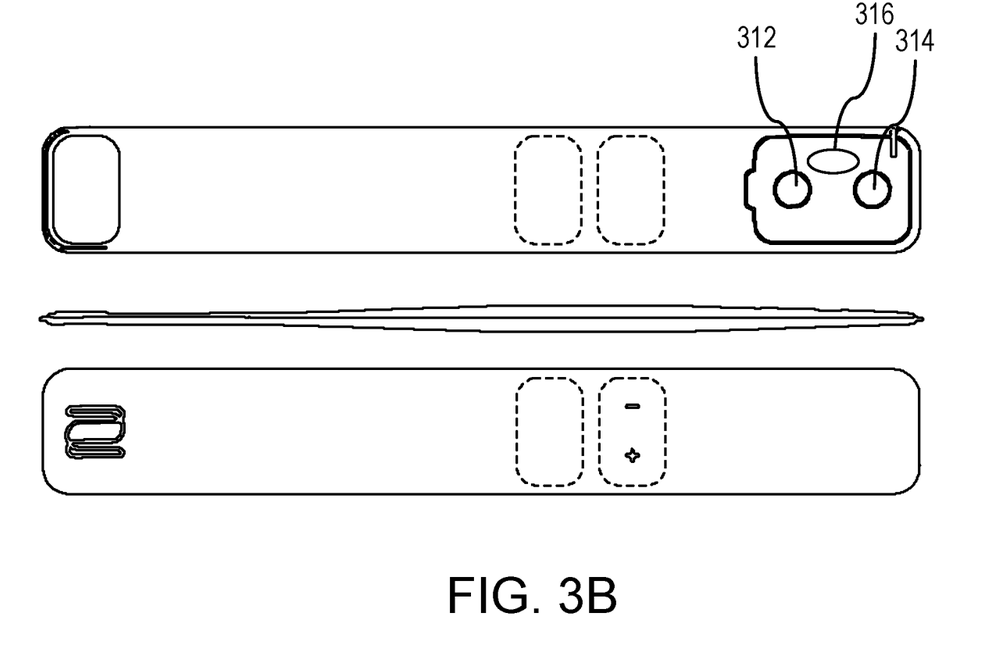
FIG. 3B depicts front, side, and back views of an example of a leg-wearable electrostimulation device.

FIG. 3B depicts front, side, and back views of an example of a leg-wearable electrostimulation device. The leg-wearable electrostimulation device can include or use a first skin electrode 312, a second skin electrode 314, and at least one auxiliary sensor 316. The auxiliary sensor can be located close to the first and second electrodes 312 & 314 such as to detect a condition at or near an electrostimulation site. Also, the auxiliary sensor can be located elsewhere on the band and relatively remote form the electrodes 312 & 314.

Figure 4:
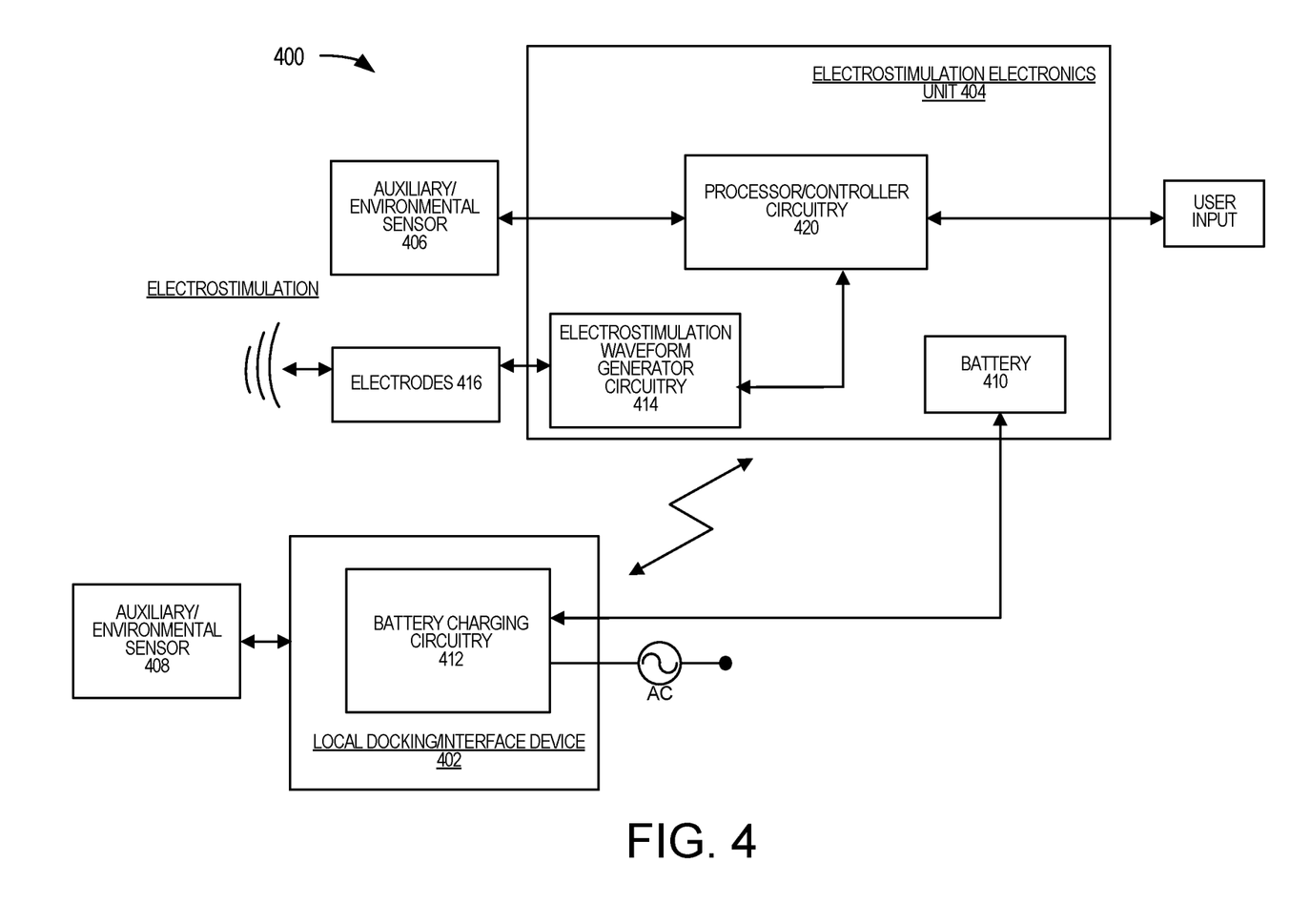
FIG. 4 schematically depicts an example of an electrostimulation system.

FIG. 4 depicts an example of an electrostimulation system. An electrostimulation system 400 can include or use an electrostimulation electronics unit 404 communicatively coupled to a local docking/interface device 402. The electrostimulation electronics unit 404 can include or use electrodes 416 for delivering a transcutaneous electrostimulation to a subject. The electrostimulation electronics unit 404 can be embedded within or coupled to a leg band, sleeve, or strap such as for holding the electrodes 416 to a treatment location. The electrostimulation electronics unit can also include or use electrostimulation waveform generator circuitry 414, a battery, and processor/controller circuitry 420. The local interface device 402 can be used local to the subject's sleep environment. The electrostimulation electronics unit 404 the local interface device 402 can include or use one or more auxiliary sensor 406 and one or more auxiliary sensor 408. As described further below, the auxiliary sensors described herein can be communicatively coupled to one or more processor circuit, such as the processor circuitry 420. In an example as depicted in FIG. 4, the local interface device 402 can be a charging station and can include or use battery charging circuitry 412. The battery charging circuitry 412 can be removably coupled to the battery 410 for a battery charging session. The local interface device 402 can also be a case, reservoir, cover, or other type of docking station for housing, maintaining, protecting, or routinely servicing the electrostimulation electronics unit.

Examples of Sleep Environment Sensors and Other Auxiliary Sensors

Figure 5:
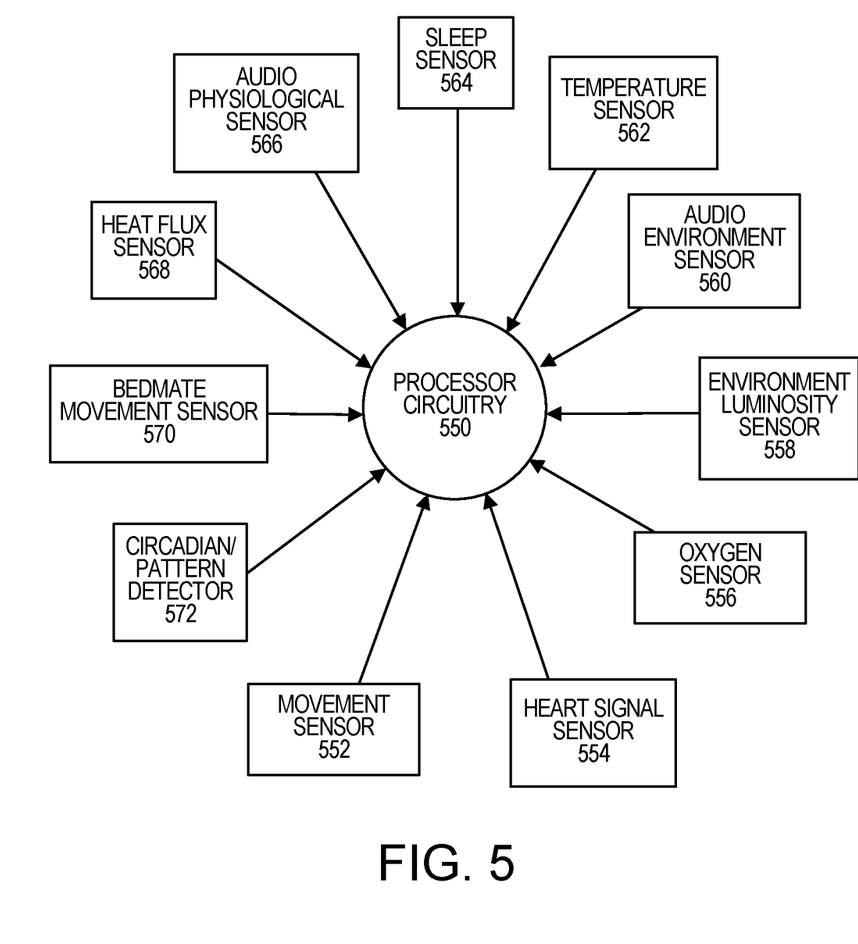
FIG. 5 depicts an example of several auxiliary sensors that can be included in an electrostimulation system.

FIG. 5 depicts an example of several auxiliary sensors that can be included in an electrostimulation system. As explained herein, one or more environment sensors or other auxiliary sensors can be included on the leg band, adhesive patch, or other wearable carrier of the electrostimulation device located on one or both legs of the subject, or included at a local docking station, smartphone, or other local interface device in the sleep environment of the subject, or elsewhere in the sleep environment of the subject. Such sensors can be communicatively coupled to one or more processor circuit, such as for collecting the environment or other auxiliary data for monitoring, analyzing, or diagnosing and generating a response based on the auxiliary data. In general, while the device can include an impedance sensor, such as for sensing skin-electrode impedance, the environment or other auxiliary sensors described herein are configured to sense auxiliary data other than skin-electrode impedance, which can be useful for various other purposes, as explained herein. Some illustrative examples are described below.

1. A position, orientation, posture, or movement sensor can include an accelerometer, a gyro, a tilt switch, or other similar sensor such as to help enable collecting auxiliary data at a location at which the leg-wearable device is worn, such as on one leg of the subject, or with separate wearables that can be located bilaterally on opposing legs of the subject. Monitoring of position, orientation, posture or movement of the patient can enable signal processing, such as by a processor circuit, for determining one or more of duration, frequency, period, or amplitude of the movement. As an illustrative example, a position sensor can be used to determine a patient's leg movement or orientation or posture, e.g., one or more upright, recumbent, lateral decubitis, left lateral decubitus, right lateral decubitus, prone, supine, or the like. Such primary information can be analyzed by a processor for determining a response. Durations in such positions, transitions between such positions, frequency of transitions, or other secondary information derived from the position, orientation, or movement sensor can be determined and used by the processor for determining a response. To the extent that the position, orientation, posture, or movement sensor includes an accelerometer or microphone responsive to a tap or pattern of taps (e.g., from a fingertip of the subject) such a sensor can additionally or alternatively be used as a user-input device, such as for starting or pausing neurostimulation in response to a specified pattern of user taps from the subject.

2. A heart signal sensor can be located on the leg-worn wearable carrier (e.g., band or adhesive patch), such as to help enable collecting auxiliary data at a location at which the leg-wearable device is worn, such as on one leg of the subject, or with separate wearables that can be located bilaterally on opposing legs of the subject. The heart rate sensor can include an optical sensor, such as a photoplethysmography (PPG) sensor, or the heart signal can be derived from a blood pressure signal, such as can use a leg-worn band of the electrostimulation device carrier in a similar manner to a blood pressure cuff, from which a blood pressure signal can be derived, and a heart rate or heart morphology signal can be determined. The heart signal can additionally or alternatively be determined using an audio sensor, such as a microphone or accelerometer, which can be used to listen for heart sounds or blood pressure audio information. The heart sensor can include electrocardiogram (ECG) electrodes and sensing amplification circuitry that can be used to sense an electrical heart rate or heart morphology signal. The heart sensor can include an impedance sensor such as to sense a cardiac stroke signal by injecting a test current and measuring a response voltage—in this context, any skin-electrode impedance that is measured is simply present as a confounding component of the impedance signal from which the cardiac stroke component is to be extracted. The heart signal sensor can be used to determine one or more of heart rate, heart signal morphology, heart rate variability (HRV), or a secondary signal that can be derived from one or more of these. For example, a respiration signal can be derived from or correlated to HRV. A sleep or sleep-stage indication can also be derived from or correlated to HRV.

3. An oxygen sensor can be located on the leg-worn wearable carrier (e.g., band or adhesive patch), such as to help enable collecting auxiliary data at a location at which the leg-wearable device is worn, such as on one leg of the subject, or with separate wearables that can be located bilaterally on opposing legs of the subject. The oxygen sensor can include an optical sensor for detecting blood oxygenation auxiliary data (e.g., blood oxygenation saturation ($SpO_2$) auxiliary data) from the leg location at which the device is worn.

4. An environment luminosity sensor can be located on a docking station, smartphone, or other local interface device in a sleep environment of the subject, such as to help detect the ambient light level, which can affect sleep. Such information can help distinguish, for example, an arousal based on a light turning on from an arousal due to RLS or PLMD. The effect of a light being on, or sleep/wake behavior of turning a light on while lying awake can be monitored, analyzed, or both.

5. An audio environment sensor, such as a microphone, can be located on the wearable(s) (e.g., worn on one or both legs) or on a docking station, smartphone, or other local interface device in a sleep environment of the subject, such as to help detect the ambient sound or noise level, which can affect sleep. Such information can help distinguish, for example, an arousal based on a loud sound from an arousal due to RLS or PLMD. The effect of ambient sound (e.g., music), or sleep/wake behavior of turning music on while lying awake can be monitored, analyzed, or both.

6. A temperature sensor, such as a thermocouple or thermometer, can be located on the wearable(s) (e.g., worn on one or both legs) or on a docking station, smartphone, or other local interface device in a sleep environment of the subject, such as to help detect body temperature or ambient room temperature, both of which can affect sleep. The body temperature or ambient room temperature can be used with one or more other monitored sleep quality metrics, such as to control an environmental variable (e.g., room temperature) or therapy parameter (e.g., neurostimulation, drug titration, CPAP, or the like) to promote or optimize sleep quality.

7. A sleep sensor can be located on the wearable(s) (e.g., worn on one or both legs) such as to help detect or correlate one or more of sleep state, sleep onset, sleep termination, sleep stage, muscle atonia associated with sleep stage, body temperature associated with sleep stage, or the like. For example, the sleep sensor may combine information from one or more or a composite information from a heart sensor, a respiration sensor, or a patient activity sensor, such as to help determine the sleep-related information or indication of interest.

8. An audio physiological sensor can be located on the wearable(s) (e.g., worn on one or both legs) such as to help detect or correlate one or more of pulmonary, cardiopulmonary, blood pressure, respiration, or other information, such as can be obtainable via a microphone, accelerometer, or other audio sensor such as can be located on the wearable.

9. A heat flux sensor can be located on the wearable(s) (e.g., worn on one or both legs) such as to help detect or correlate one or more of peripheral circulatory functional information, such as vasodilation or vasoconstriction, such as may play a role in sleep quality and may be monitored or used for adjusting or recommending a therapy protocol (e.g., neurostimulation, CPAP, drug regimen, or other sleep-related therapy or protocol).

10. A bedmate movement sensor can be located on a docking station, smartphone, or other local interface device in a sleep environment of the subject, such as to help detect the movement of a bedmate (e.g., a person or pet sharing a bed or sleeping area with the subject, that is, some person or animal other than the subject), which can affect sleep. In an example in which both the subject and the bedmate are provided with wearable devices, the information about movement of the bedmate can be generated by a wearable worn by the bedmate (e.g., leg-worn, wrist-worn, or another device worn by the bedmate).

11. Circadian or other pattern detector can use information from one or more other physiologic auxiliary sensors, such as can be collected over a period of time and stored and analyzed for the presence of a circadian or other pattern that can be useful in recommending or adjusting a therapy or generating another response to such information.

In an example in which the wearables include a pair of wearable leg band or adhesive patch neurostimulation device carriers, data from the auxiliary sensors on each of the subject's left and right legs can be temporally synchronized such as for signal-processing analysis by the processor componentry, such as for providing one or more responses, such as described herein. Using bilateral auxiliary sensor data, as opposed to auxiliary sensor data from an auxiliary sensor on one leg, can allow correlation between auxiliary data on the different legs to filter out noise factors—such as the leg movements that are present in the RLS or PLMD patients wearing the wearable devices at the leg-worn locations of interest. This can obviate the need for a wrist-worn device, and appropriate noise-filtering of the leg movements, together with the bilateral auxiliary data stream, can help provide adequate auxiliary information relevant to sleep monitoring or one or more forms of sleep therapy.

Examples of Responses to Environmental or Other Auxiliary Sensor Data

Figure 6:
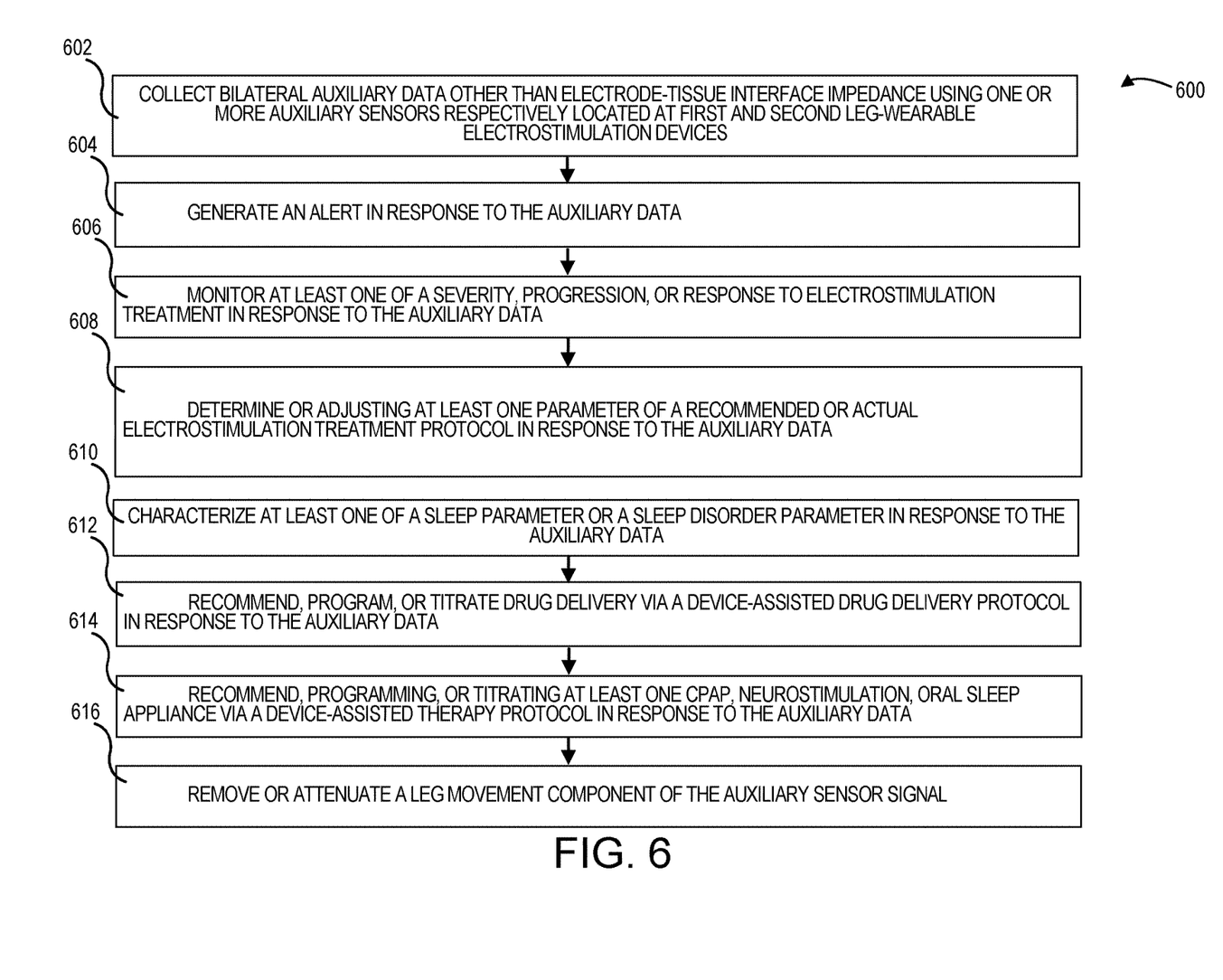
FIG. 6 is a flowchart of a method of using an example of an electrostimulation system.

FIG. 6 is a flowchart of a method of using an example of an electrostimulation system. At 602, auxiliary data can be collected using one or more auxiliary sensors located respectively at one of the leg-wearable electrostimulation devices. The auxiliary data can be data other than electrode-tissue interface impedance. In an example, Bilateral auxiliary data can be collected using one or more auxiliary sensors respectively located at first and second leg-wearable electrostimulation devices. The auxiliary sensor data can be provided to a processor, such as for monitoring, analysis, diagnosis, signal-processing, storage, or generating a response. Illustrative non-limiting examples of responses can include:

At 604, Generating an alert to the subject or a caregiver, e.g., via a local or remote user interface device coupled to the processor, such as can be helpful toward the goal of improving sleep. The alert may be contemporaneous, or it may be delayed so as not to interfere with sleep by providing the alert.

At 606, Monitoring can include storing auxiliary data or information derived therefrom, such as for monitoring at least one of a severity or a progression of a sleep disorder or other sleep condition, or of an auxiliary physiologic response to electrostimulation treatment. In an example, the auxiliary physiologic response to electrostimulation constitutes something other than (or in addition to) an evoked response to neurostimulation or an EMG sensor response to neurostimulation from an auxiliary sensor located on the wearable.

At 608, Determining or adjusting at least one electrostimulation parameter of a recommended or actual electrostimulation treatment protocol (e.g., amplitude, frequency, duration, electrode selection, ramping, or any setting of one or more other neurostimulation parameter).

At 610, Characterizing at least one of a sleep parameter or a sleep disorder parameter. This can include, for example, characterizing one or more of sleep state, sleep stage, sleep quality, OSA degree, CSA degree, OSA vs. CSA, arousal frequency, arousal duration, physiological or environmental factors correlated to the sleep or arousal parameter, or the like.

At 612, Recommending, programming, or titrating drug delivery via a device-assisted drug delivery protocol. This can include, for example, dosage amount, dosing frequency, dose ramp-up or ramp-down, logging a history of environment or other auxiliary parameters or correlation with drug delivery, or the like, such as via a smartphone application or other user-interface device for the subject or a caregiver.

At 614, Recommending, programming or titrating at least one of CPAP, neurostimulation, oral sleep appliance via a device-assisted therapy protocol. This can include, for example, for one or more such non-drug therapy, non-drug therapy amount, therapy frequency, therapy ramp-up or ramp-down, logging a history of environment or other auxiliary parameters or correlation with non-drug therapy delivery, or the like, such as via a smartphone application or other user-interface device for the subject or a caregiver.

And, at 616, Removing or attenuating a leg movement component of the auxiliary sensor signal. As described further below, electrostimulation systems described herein can include or use various mechanisms such as to mitigate noise from the data. For example, a subject having one or more symptoms of RLS can produce leg movement which can be challenging to interpret from data collected by one or more movement sensors. Other sensor-inputs can be used such as to attenuate this signal or remove this leg movement component from an analysis of data collected by the auxiliary sensors.

Use of Additional Sensors to Measure Objective Metrics Relating to Sleep

1. Activity and motion sensing. The system can include or use additional sensors such as an accelerometer, a gyroscope or inertial measurement unit (IMU) to measure activity. While traditional actigraphic sensors record absence of motion to impute sleep states and stage them, patients suffering from Restless Legs Syndrome (RLS) may have unique physiological differences that makes it difficult to do the same without accounting for natural periodic leg movements (PLMs) or other voluntary leg movements (such as rubbing feet together, kicking legs, stretching, dorsiflexion) that RLS patients often repeat constantly through the night, sometimes even when in light sleep. Such movements may falsely register as wakefulness when they are not accounted for. Further to this, the system can allow for a treating physician to only see movement that is relevant to arousals from sleep, as opposed to movements that may have been involuntary or otherwise unimpactful to sleep quality. This may be derived from a combination of processed data from both legs along with movement data from the bedside dock. As an example, it may be the case that only side-to-side turns during sleep cause an actual arousal (as measured by surface EEG) and other leg movements may be unimpactful to sleep. The on-board gyroscope allows for detection of rotational movement and distinguishes these from leg movements detected by the accelerometer.

2. Heart Rate and sympathetic tone. The system could include measurement of average heart rate using a PPG sensor, or by directly coupling ECG signal from the hydrogel stimulation electrodes. Measurement of heart rate, or ECG is often complicated by movement artifacts and noise and in the case of PPG sensors, skin tone as well. Our system presents a unique advantage in that the bedside base station can process data from the bilateral devices worn on both legs to time synchronize, average, and obtain a more reliable background heart rate even when individual sensor data may appear to be noisy. The use of the bedside dock further allows for motion cancelation (by sensing patient movement using a camera, infrared or electromagnetic signal emitted).

3. Spo2/Oxygenation. The system could include the measurement of oxygen saturation in the blood, an important marker relating to severity of conditions such as obstructive sleep apnea but also a potential key marker for poor circulation in the periphery. The system allows for synchronizing dynamic data from two legs at the same time via communication with the bedside base station and would employ the same motion canceling algorithms that benefit ECG and HR measurement described above in (2). The proposed skin surface over which the device is worn on the legs is rich with blood supply and serves as a prime target to measure oxygen saturation. Patients with RLS may also present with undiagnosed or otherwise poorly controlled sleep apnea, and the data presented to the physician would allow for accurately identifying these conditions that may be severely detrimental to the patient's health in the long-term.

4. Audio-based sensors. Use of an on-board microphone allows for detection of snoring or other apnea-related sounds. The microphone may be placed on the bedside charging dock and the use of this additional channel of data could further help refine sleep staging. The use of a microphone also allows the system to account for any ambient or background noises and their decibel level to correlate to sleep quality impacts.

5. Light sensors. Use of a photodetector or light sensor allows for the system to accurately tell when the patient attempts to fall asleep, an important metric to assess sleep onset latency. Most other methods rely purely on subjective patient reports to record when a patient went to bed. The use of an on-board light sensor either on the bands or the dock (or both) allows for the use of a combination of light, sound, and motion to accurately make a determination of time at which patient goes to bed without relying on subjective patient reports.

6. Environment sensors. Use of a thermistor (temperature sensor) and humidity sensor allows the system to further record environmental conditions around the use of the devices. This closely ties in to interpreting metrics that may negatively or positively impact sleep quality and can be used to coach and improve sleep hygiene and therefore sleep quality.

The above description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round," a component that is not precisely circular (e.g., one that is slightly oblong or is a many-sided polygon) is still encompassed by this description.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A system for monitoring or treating at least one of Restless Leg Syndrome (RLS) or Periodic Limb Movement Disorder (PLMD), the system comprising:
   a first leg-wearable electrostimulation device for continuously or intermittently acquiring auxiliary data from a subject at a first leg location at which the device is worn, the first leg-wearable electrostimulation device comprising:
      a first neurostimulation delivery device, configured for delivering transcutaneous neurostimulation therapy to a leg of the subject to treat at least one of RLS or PLMD via first and second skin electrodes at the first leg location; and
      at least one auxiliary sensor, including at least one of a blood oxygenation sensor, a pulse oximeter, an optical heart sensor, a photoplethysmography (PPG) sensor, an audio physiological sensor, an audio environment sensor, a temperature sensor, a heat flux sensor, a bedmate movement sensor, an environment luminosity sensor, or a circadian/pattern detector, the at least one auxiliary sensor configured for detecting the auxiliary data other than electrode-tissue interface impedance at the first leg location at which the device is worn;
   wherein the first neurostimulation delivery device is configured to receive a response, based at least in part on the auxiliary data, to establish or adjust at least one electrostimulation waveform parameter for delivery at the first leg location; and
   wherein the at least one auxiliary sensor is configured for detecting a sleep quality indicator or an RLS or PLMD therapy efficacy indicator following the response to establish or adjust the at least one electrostimulation waveform parameter.

2. The system of claim 1, wherein the at least one auxiliary sensor includes at least one of a position, orientation, or movement sensor configured for detecting at least one of position, orientation, or movement auxiliary data from the leg location at which the device is worn.

3. The system of claim 1, wherein the at least one auxiliary sensor includes a blood oxygenation auxiliary sensor configured for detecting blood oxygenation auxiliary data from the leg location at which the device is worn.

4. The system of claim 3, wherein the blood oxygenation auxiliary sensor includes a pulse oximeter for detecting blood oxygenation saturation (Sp02) auxiliary data from the leg location at which the device is worn.

5. The system of claim 1, wherein the at least one auxiliary sensor includes a heart signal sensor configured for detecting heart signal auxiliary data from the leg location at which the device is worn.

6. The system of claim 5, wherein the heart signal sensor includes an optical sensor.

7. The system of claim 5, wherein the heart signal sensor includes a photoplethysmography (PPG) sensor.

8. The system of claim 1, further comprising processor componentry included in or communicatively coupled to the first leg-wearable electrostimulation device, the processor configured to perform encoded instructions to at least one of monitor, analyze, or diagnose auxiliary data collected from the first leg-wearable electrostimulation device over a period of time.

9. The system of claim 8, wherein the processor is configured to, based at least in part on the auxiliary data, perform encoded instructions to provide the response including at least one of:
   generating an alert;
   monitoring at least one of a severity, progression, or response to electrostimulation treatment;
   determining or adjusting at least one parameter of a recommended or actual electrostimulation treatment protocol;
   characterizing at least one of a sleep parameter or a sleep disorder parameter;
   recommending, programming, or titrating drug delivery via a device-assisted drug delivery protocol; or
   recommending, programming or titrating at least one of CPAP, neurostimulation, oral sleep appliance via a device-assisted therapy protocol.

10. The system of claim 9, wherein the at least one of the sleep parameter or the sleep disorder parameter corresponds to at least one of obstructive sleep apnea (OSA), central sleep apnea (CSA), REM sleep behavior disorder, narcolepsy, circadian rhythm sleep disorder, circadian misalignment, jet lag, sleepwalking, insomnia, or parasomnia.

11. The system of claim 1, further comprising a second leg-wearable electrostimulation device for continuously or intermittently acquiring auxiliary data from a subject at a second leg location at which the second leg-wearable electrostimulation device is worn on a different leg from the first leg-wearable electrostimulation device, the second leg-wearable electrostimulation device comprising:

a second neurostimulation delivery device, configured for delivering transcutaneous neurostimulation therapy to the different leg of the subject to treat at least one RLS or PLMD; and a second auxiliary sensor, configured for detecting auxiliary data other than electrode-tissue interface impedance at the second leg location at which the second leg-wearable electrostimulation device is worn.

12. The system of claim 1, wherein the at least one auxiliary sensor comprises at least one of:
a body temperature sensor;
a body posture or position sensor;
a peripheral circulatory function sensor;
a heat-flux sensor, configured for at least one of monitoring, detecting, or analyzing at least one of vasodilation or vasoconstriction; or
an audio sensor, configured for at least one of monitoring, detecting, or analyzing an indication of pulmonary function, blood pressure, or presence or detected movement of a bedmate.

13. The system of claim 1, further comprising a docking station or other local interface device communicatively coupled with at least the first leg-wearable electrostimulation device, the local interface device comprising at least one environment sensor for collecting environment data of a sleep environment of the subject.

14. The system of claim 13, wherein the environment data includes at least one of luminosity, temperature, audio, or motion of a bedmate or other movement in the sleep environment of the subject.

15. The system of claim 1, wherein the at least one auxiliary sensor includes at least one of a pulse oximeter, an optical heart sensor, a photoplethysmography (PPG) sensor, or an audio physiological sensor.

16. A system for monitoring or treating at least one of Restless Leg Syndrome (RLS) or Periodic Limb Movement Disorder (PLMD), the system comprising:
a first leg-wearable electrostimulation device for continuously or intermittently acquiring auxiliary data from a subject at a first leg location at which the device is worn, the first leg-wearable electrostimulation device comprising:
a first neurostimulation delivery device, configured for delivering transcutaneous neurostimulation therapy to a leg of the subject to treat at least one of RLS or PLMD via first and second skin electrodes at the first leg location; and
a first auxiliary sensor, configured for detecting the auxiliary data other than electrode-tissue interface impedance at the first leg location at which the device is worn for providing a response based at least in part on the auxiliary data;
a second leg-wearable electrostimulation device for continuously or intermittently acquiring auxiliary data from a subject at a second leg location at which the second leg-wearable electrostimulation device is worn on a different leg from the first leg-wearable electrostimulation device, the second leg-wearable electrostimulation device comprising:
a second neurostimulation delivery device, configured for delivering transcutaneous neurostimulation therapy to the different leg of the subject to treat at least one RLS or PLMD; and
a second auxiliary sensor, configured for detecting auxiliary data other than electrode-tissue interface impedance at the second leg location at which the second leg-wearable electrostimulation device is worn; and
processor componentry configured for temporally aligning auxiliary data received from the first and second auxiliary sensors for providing temporally-aligned bilateral auxiliary data.

17. A system for monitoring or treating at least one of RLS or PLMD of a subject in a sleep environment, the system comprising:
first and second leg-wearable electrostimulation devices for continuously or intermittently acquiring auxiliary data other than electrode-tissue interface impedance from a subject at respective first and second leg locations at which the device is worn bilaterally on opposing legs, wherein each of the first and second leg-wearable electrostimulation devices comprises:
a neurostimulation delivery device, configured for delivering transcutaneous neurostimulation therapy to a leg of the subject to treat at least one of RLS or PLMD via first and second skin electrodes at each of the first and second leg locations; and
at least one auxiliary sensor, including at least one of a blood oxygenation sensor, a pulse oximeter, an optical heart sensor, a photoplethysmography (PPG) sensor, an audio physiological sensor, an audio environment sensor, a temperature sensor, a heat flux sensor, a bedmate movement sensor, an environment luminosity sensor, or a circadian/pattern detector, the at least one auxiliary sensor configured for bilaterally detecting the auxiliary data from the respective first and second leg locations at which the first and second leg-wearable electrostimulation devices are worn
wherein the neurostimulation delivery device is configured to receive a response, based at least in part on the auxiliary data, to establish or adjust at least one electrostimulation waveform parameter for delivery to at least one of the first and second leg locations; and
wherein the at least one auxiliary sensor is configured for detecting a sleep quality indicator or an RLS or PLMD therapy efficacy indicator following the response to establish or adjust the at least one electrostimulation waveform parameter.

18. The system of claim 17, further comprising a local interface device communicatively coupled with the first and second leg-wearable electrostimulation devices, the local interface device comprising at least one environment sensor for collecting environment data of the sleep environment.

19. A device-assisted method for monitoring or treating a subject receiving transcutaneous neurostimulation therapy in a sleep environment, the method comprising:
collecting auxiliary data other than electrode-tissue interface impedance, the collecting including using one or more auxiliary sensors respectively located at one or more leg-wearable electrostimulation devices, including collecting at least one of blood oxygenation, pulse oximetry, optical heart sensor, photoplethysmography (PPG), audio physiology, audio environment, temperature, heat flux, bedmate movement, environment luminosity, or circadian/pattern data;
generating a response to the auxiliary data, including establishing or adjusting at least one electrostimulation waveform parameter for delivery to an external leg location at which the electrostimulation device is worn; and
detecting at least one RLS or PLMD therapy efficacy indicator, via the one or more auxiliary sensors, following the establishing or adjusting the at least one electrostimulation waveform parameter.

20. The method of claim 19, wherein generating the response to the auxiliary data includes at least one of:
   generating an alert;
   monitoring at least one of a severity, progression, or response to electrostimulation treatment;
   determining or adjusting at least one parameter of a recommended or actual electrostimulation treatment protocol;
   characterizing at least one of a sleep parameter or a sleep disorder parameter; or
   recommending, programming, or titrating drug delivery via a device-assisted drug delivery protocol; or recommending, programming or titrating at least one of CPAP, neurostimulation, oral sleep appliance via a device-assisted therapy protocol.

21. The method of claim 19, wherein generating the response to the auxiliary data is also based at least in part on collected environment data about a sleep environment of the subject.

\* \* \* \* \*